United States Patent
Hayashizaki

(10) Patent No.: US 6,841,055 B2
(45) Date of Patent: Jan. 11, 2005

(54) METHOD OF PREPARING ELECTROPHORETIC SUPPORT, ELECTROPHORETIC MATRIX, AND METHOD OF ELECTROPHORESIS

(75) Inventor: Yoshihide Hayashizaki, Ibaraki (JP)

(73) Assignee: Riken, Wako (JP)

(*) Notice: Subject to any disclaimer, the term of this patent is extended or adjusted under 35 U.S.C. 154(b) by 334 days.

(21) Appl. No.: 09/852,800

(22) Filed: May 11, 2001

(65) Prior Publication Data

US 2002/0033338 A1 Mar. 21, 2002

Related U.S. Application Data

(63) Continuation of application No. PCT/JP00/06247, filed on Sep. 13, 2000.

(30) Foreign Application Priority Data

Sep. 13, 1999 (JP) .............................................. 11-259013

(51) Int. Cl.$^7$ ............................................. G01N 27/447
(52) U.S. Cl. ...................... 204/456; 204/466; 204/470; 204/455
(58) Field of Search ..................... 134/6; 526/303.1; 204/456, 466, 469, 470, 451, 450, 455

(56) References Cited

U.S. PATENT DOCUMENTS 4,213,873 A * 7/1980 Church ....................... 510/400
5,066,376 A * 11/1991 Osterhoudt et al. ........... 204/470
6,013,331 A * 1/2000 Ogawa ......................... 427/515
6,533,914 B1 * 3/2003 Liu ............................. 204/601

OTHER PUBLICATIONS

Anthony Andrews, Electrophoresis: Theory, Techniques, and Biochemical and Clinical Applications, $2^{nd}$. Clarendon Press–Oxford, 1986, pp. 26–27.*

Luckey et al., J. Phy. Chem., vol. 97, No. 12 (1993) pp. 3067–3075.

Ganzler et al., Anal. Chem., vol. 64 (1992) pp. 2665–2671, Nov.

Tsuji, J. Chromatography, vol. 550 (1991) pp. 823–830.

Karger, Electrophoresis, vol. 17 (1996) pp. 144–151.

* cited by examiner

Primary Examiner—Alex Noguerola
(74) Attorney, Agent, or Firm—Birch, Stewart, Kolasch & Birch, LLP

(57) ABSTRACT

A method of preparing an electrophoretic support comprising washing of at least a portion of the surface of a silicon-containing support member supporting an electrophoretic matrix with a weak alkali solution and supporting of said matrix by said support member; an electrophoretic gel comprising a polyacrylamide polymer obtained by polymerizing acrylamide or a derivative thereof in the presence of two or more polar organic solvents; a method of electrophoresis employing a gel prepared by said preparation method; and a method of electrophoresis employing said electrophoretic gel.

20 Claims, No Drawings

METHOD OF PREPARING ELECTROPHORETIC SUPPORT, ELECTROPHORETIC MATRIX, AND METHOD OF ELECTROPHORESIS

This application is a Continuation of PCT International Application No. PCT/JP00/06247 filed on Sep. 13, 2000, which was not published in English and which designated the United States and on which priority is claimed under 35 U.S.C. § 120, the entire contents of which are hereby incorporated by reference.

TECHNICAL FIELD

The present invention relates to a method of preparing an electrophoretic support, an electrophoretic matrix, and a method of electrophoresis. More particularly, the present invention relates to a method of preparing an electrophoretic support in which an electrophoretic matrix such as a gel or an entangled polymer is formed on a silicon-containing support member, a method characterized by how the support member is cleaned, and a method of electrophoresis employing the support prepared by this method. The present invention further relates to an electrophoretic gel employed to separate nucleic acids or PNA fragments and to a method of separating nucleic acids or PNA fragments employing this gel or this support.

The method of preparing an electrophoretic support of the present invention inhibits the generation of bubbles during the formation of electrophoretic matrices and thus improves sample (for example, nucleic acid) separation performance. Further the electrophoretic method employing the electrophoretic support or gel of the present invention increases separation performance in electrophoresis. Thus, the separation of long strands of nucleic acid and PNA fragments required by sequencing methods in particular is readily performed, and the present invention is particularly useful when applied to methods of long-strand nucleotide sequencing.

TECHNICAL BACKGROUND

Analysis of the nucleotide sequence of the human genome, said to comprise as many as three billion base pairs, is progressing. In particular, the analysis of polymorphism in the human genome relates to the unique traits of each individual and is the subject of considerable interest in the fields of medicine, pharmacology, and biology. Conventionally, the development of a sequencer capable of automatically processing multiple samples simultaneously, rapidly, and with high sensitivity has been conducted to determine the huge nucleotide sequence of the human genome. In particular, the arrival of multicapillary DNA sequencers simultaneously employing multiple capillary columns packed with gel instead of the tabular slab gel that was previously employed has greatly contributed to increasing the speed of nucleotide sequencing. Currently, 96 capillary column (for example, the Sequencer 3700 from ABI and the MegaBACE 1000 from Molecular Dynamics), and recently, the fourfold 384 capillary column (the development of the 384 multicapillary sequencing system: Proceedings of the 21$^{st}$ Meeting of the Japan Molecular Biology Society, 1P-570 (Yokohama, December 1998) multicapillary DNA sequencers have been developed.

However, when the number of capillary columns is increased, there are limitations due to the performance and structure of the detection devices used to read the sequences. Further, merely increasing the number of capillary columns does not diminish the labor required to supply the capillary columns themselves and to load specimens into capillary columns.

Further, in currently employed sequencers, about 500 bases are read by a single capillary column. Increasing the number of bases read by a single capillary column to increase separation performance has the advantage of reducing the effort required to supply the capillary columns themselves and to load specimens into the capillary columns. However, almost no studies have been conducted into reading more bases at once in individual capillary columns; this remains a problem to be solved in the future.

For example, in many electrophoretic devices including DNA sequencing devices, a support member is employed to support the electrophoretic matrix. The support member has various shapes depending on the electrophoretic objective. For example, in slab electrophoresis, two pieces of flat tabular silica glass are employed. In capillary electrophoresis, a column-shaped (hollow tubular) silicate capillary column is employed as the support member. Further, in micro electrophoresis, a support member with minute separation passages formed on a silicon wafer is employed. All of these support members are generally made of silicon-containing materials, such as silica.

To obtain good separation performance in electrophoretic matrices prepared on such silicon-containing support members (referred to hereinafter as simply "support members"), it is desirable for bubbles not to be present in the matrix.

For example, when electrophoretic gel is sandwiched between two support members (in slab electrophoresis), when an entangled polymer solution is injected into a cavity in a support member (capillary electrophoresis), or when a support member is employed without being cleaned, particularly when the width of the support member or injection inlet are narrow (when the width is less than about 1 mm in diameter), air bubbles tend to develop near the surface and in the minute voids of the support member. Gel and entangled polymer matrices containing such bubbles do not provide adequate separation performance and cannot perform the original functions of electrophoretic matrices.

The method of admixing propanol or polyethylene glycol in advance to polymerization has been proposed as a method of preventing the development of such bubbles (Anal. Chem., 1992, 64, pp. 2665–2671; J. Chromatogr., 1991, 550, pp. 823–830). This method yields a matrix that does not contain bubbles. However, the support obtained by this method has the drawback of having lower separation performance in electrophoresis than conventional supports. Thus, this method is unsuitable for electrophoresis requiring high separation performance.

Further, assuming that impurities present on the surface of the support member are the cause of the bubbles, attempts at inhibiting the occurrence of bubbles have been made by the method of cleaning away impurities on the inner walls of capillary columns using a strong base solution such as NaOH, organic solvents such as ethanol, acid solutions such as HCl, and solutions of these compounds in combination by using pure water (Electrophoresis 1996, 17, pp. 144–151). However, although this method prevents the occurrence of bubbles at the surface of the support member, electrophoretic separation performance is unsatisfactory in the same manner as in the above-described method.

Accordingly, there has been for some time a need to provide a method of preparing electrophoretic supports capable of effectively inhibiting the occurrence of bubbles in matrices carried by or packed in support members that deliver good separation performance.

Further, in addition to methods of preparing electrophoretic supports, there has also been room for improvement in the electrophoretic matrix itself to improve electrophoretic separation performance, However, there has not been adequate investigation of electrophoretic matrix materials and the like.

Accordingly, the object of the present invention is to provide a means of solving the above-stated problems in electrophoresis, improving electrophoretic separation performance, improving sample separation, and particularly, in nucleic acid and PNA fragments, reading even longer-strand nucleotide sequences.

More specifically, the object of the present invention is to provide a method of preparing an electrophoretic support capable of fin inhibiting the generation of bubbles in the matrix when preparing an electrophoretic support employing a silicon-containing support member, and to provide a method of electrophoresis employing the electrophoretic support prepared by this method.

A further object of the present invention is to provide an electrophoretic gel tending not to undergo compression in the nucleotide sequencing of long-strands exceeding 500 bases, and to provide a method of electrophoresis capable of reading long-strand nucleotide sequences using this gel.

DISCLOSURE OF THE INVENTION

The present inventors conducted extensive research into methods of preparing supports capable of improving separation performance without generating bubbles in the course of supporting (carrying or filling) a matrix such as a gel or a polymer with a silicon-containing support member such as a silica capillary column.

As set forth above, the generation of bubbles in the support can be inhibited by cleaning the support member with a strong alkali solution, but despite the inhibition of the formation of bubbles, separation performance does not improve. The present inventors presumed that it was caused by the support member surface being etched by the action of the strong alkali reagent, creating irregularities in the surface of the support member. As a result, dispersion in directions other than the direction of separation of electrophoresis occurs, or the number of free silanol moieties increase at the surface of the support member, preventing improvement in separation performance in electrophoresis.

Accordingly, the present inventors, based on these presumptions, examined various methods in which the etching of the surface of the support member tended not to be etched and the generation of bubbles tended not to occur in the matrix. As a result, they discovered that bubbles are not generated in a matrix that is supported (carried or filled) by a support member that has been cleaned with a weak alkali solution, and that separation performance during electrophoresis improves relative to conventional methods employing strong alkali solutions; the present invention (method of preparing an electrophoretic support) was devised on that basis.

That is, the first mode of implementing the present invention relates to a method of preparing an electrophoretic support wherein at least one portion of the surface of a member (hereinafter "support member") for supporting an electrophoretic matrix and coming into contact with said matrix is washed, and said matrix is then supported by said support member, characterized in that said support member comprises a silicon-containing material and at least a part of said washing is conducted with a weak alkali solution.

The second mode of implementing the present invention relates to a method of electrophoresis employing an electrophoretic matrix prepared by the above-described method of preparation.

Further, the present inventors investigated the separation of longer strands of nucleic acid or PNA fragments than in the past at one time in one carrier column to a degree permitting nuclectide sequencing, and as a result, improvement in the composition of the electrophoretic gel in a manner permitting nucleotide sequencing was made, as well as the electrophoretic conditions employed when using this gel, and, in particular, electrophoretic solutions were investigated.

Polyacrylamide gel is generally employed in electrophoresis for nucleotide sequencing (reference: PACE (polyacrylamide gel electrophoresis), Hirokawa Shoten, 1990, ed. by Toshio TAKAGI). The present inventors discovered that a gel obtained by preparing a polyacrylamide gel in the presence of two or more polar organic solvents, such as methanol and formamide, solved the above-stated problems; the present invention (electrophoretic gel) was devised on this basis.

That is, the third mode of the present invention relates to an electrophoretic gel comprising a polyacrylamide polymer obtained by polymerizing an acrylamide, or a derivative thereof, in the presence of two or more polar organic solvents.

The fourth mode of the present invention relates to a method of separating nucleic acids or PNA fragments by electrophoresis in the presence or a polar organic solvent.

A highly flexible gel obtained by polymerization in the presence of a water-soluble polymer such as dextran can be employed as the gel of the third mode of the present invention (Katsunori AIZAWA, Tanpakushitu-kakusan-koso 43 (1998) 2191–2198).

Most Preferred Modes of Practicing the Present Invention
Method of Preparing an Electrophoretic Support (Mode 1)

In the method of preparing an electrophoretic support of the present invention, a support member comprising a silicon-containing material is employed to support the matrix. The support member employed here is not specifically limited as to material so long as it contains at least silicon and can be employed in electrophoresis. Examples of the materials of such silicon-containing support members are natural and synthetic silica, borosilicate glass, alkali lead glass, soda lime silica glass and other glass products, quartzite bricks, zeolite, cordierite, silicon carbonate, silicon, enamel, and other compounds chiefly comprised of silicon.

The shape of the support member employed in the present invention may be suitably determined based on what is to be separated. Examples of shapes are tabular, columnar (hollow cylinder), granular, fiber-like, and any combination thereof. Further, any wafer of any shape functioning as a chip in microchip electrophoresis and nanochip electrophoresis is covered by the support member of the present invention.

The diameter and length of the support member may be suitably determined based on the object of separation. For example, in the case of a capillary column, an outer diameter of 100–400 $\mu$m, an inner diameter of 2–100 $\mu$m and a length of about 10–100 cm are appropriate. When conducting measurement with fluorescent light with a sequencer in capillary columns, it is desirable to employ a material or a support member that has been processed (coated with a nonfluorescent substance) so as not to interfere with fluorescent measurement.

The surface of the support member of the present invention coming into contact with the electrophoretic gel is washed with a weak alkali solution. The weak alkali solution employed in washing is a liquid solution with a solute in the form of a weak alkali substance (including organic substances and inorganic substances), preferably one dissolved in water.

Examples of modes of the weak alkali solutions are organic solutions, inorganic solutions, and mixtures comprising any combination of organic solution and inorganic solution.

Examples of organic solutions are solutions comprising an organic compound, or a combination of multiple organic compounds, selected from the group consisting of aminobutanoic acid, 2-amino-2-ethyl-1,3-propanediol, 2-amino-2-methyl-1,3-propanediol, 2-amino-2-methyl-1-propanol, aminopyridine, butylamine, chloridine, diethanolamine, diethylamine, diethylbarbituric acid, dimethylamine, dimethylimidazole, ephedrine, ethanolamine, ethylmorpholine, glycylglycine, hydroxypyroline, piperidine, propylamine, methylamine, methylimidazole, triethylamine, triethanolamine, trimethylamine, tris (hydroxymethyl)aminomethanol dissolved in a solvent. For example, when dissolved in a solvent at room temperature, the pK value is 7–12 and the pH value is 7–12, preferably 8–11.

Further examples of organic solutions in addition to the above are solutions of organic compounds such as amines, amides, imides, ammonia compounds, and amino acids, and solutions in ammonia water and "Good" buffer solutions, where a slightly alkaline pH is exhibited when the solutions are prepared, as well as solutions adjusted to slight alkalinity with a reagent.

Examples of inorganic solutions are substances selected from among the group consisting of phosphoric acid, pyrophosphoric acid, boric acid, and carbonic acid, exhibiting a pK of 7–12 at room temperature, and when the inorganic compounds are in solution, a weakly alkaline pH (a pH of 7–12, preferably 8–11); solutions prepared to be slightly alkaline with reagents are also included. The inorganic solution of preference is an aqueous solution of carbonate.

The weakly alkaline solution employed in washing in the present invention may also comprise any concentration of mixed-in organic solvent.

In the washing of the present invention, at lease one part of the washing is conducted with an alkaline solution. That is, in the washing of the present invention, it is possible to use other solutions in combination with the weakly alkaline solution. Examples of other solutions that may be employed in combination are: pure water (milli-Q processed pure water) and other neutral solutions; methanol, ethanol, and other organic solvents; and solvents obtained by combining a weakly alkaline solution and a weakly acid solution. The order of washing when employing a solution in addition to the weakly alkaline solution is not specifically limited so long as the washing with a weakly alkaline solution is not omitted; washing with a weakly alkaline solution may be conducted at any step such as first or last. The washing with a solution other than a weakly alkaline solution may be omitted for any reason.

Any time falling within several seconds to several months may be selected as the washing time. However, in consideration of efficiency of operation and the like, a washing time of about several minutes is desirable. The temperature during washing is not specifically limited so long as the solution does not solidify, volatize, or boil away. Washing at room temperature is desirable from the perspective of facilitating the operation.

In the present invention, at least a portion of the surface of the support member coming into contact with the electrophoretic matrix is washed. Since the washing of the support member is conducted with the object of inhibiting the formation of bubbles during preparation of the electrophoretic matrix, the entire surface of the support member coming into contact with the electrophoretic matrix is desirably washed.

Matrices generally employed in electrophoresis can be employed without alteration as the electrophoretic matrix coming into contact with the support member. The matrix may comprise a gel or an entangled polymer, but is not specifically limited thereto. Examples of matrices are polyacrylamide, agarose gel, and entangled polymers having a molecular sieving function such as straight-chain polyacrylamides, water-soluble cellulose derivatives, and dextran. The electrophoretic gel of the present invention that is described as such a matrix further below may also be employed. The use of this gel is suited to the separation of nucleic acids and PNA fragments.

In addition, the methods and conditions that are generally employed for matrices can be employed as the methods and conditions for making and filling matrices in the preparation of electrophoretic matrices coming into contact with the support member. Further, when the matrix is the electrophoretic gel of the present invention, described further below, it can be prepared according to the conditions described further below.

Method of Electrophoresis Employing a Matrix Prepared by the Preparation
Method of the Present Invention (Mode 2)

The present invention covers the method of electrophoresis employing a matrix prepared by the preparation method of the present invention. Based on this method of electrophoresis, various substances can be separated based on the matrix employed in electrophoresis. Examples of such substances are water-soluble substances comprising one, two, or more cationic and/or anionic charges, neutral substances not having a charge, and any mixture thereof. Nucleic acids (DNA and RNA) and PNA fragments are included therein. Additionally, organic substances, inorganic substances (including metal ions), and substances comprising combinations thereof are also included in the above-mentioned substances. A suitable form of the substance to be separated such as a solid, slurry, powder, or liquid may be suitably selected based on the matrix and electrophoresis conditions.

The conditions of electrophoresis such as the buffer solution, voltage, and time employed in the method of electrophoresis of the present invention are suitably selected based on the characteristics of the matrix and the substance to be separated. The conditions of electrophoresis employed when the matrix is the electrophoretic gel of the present invention described further below may also be employed.

Electrophoretic Gel (Mode 3)

The electrophoretic gel of the present invention comprises a polyacrylamide polymer obtained by polymerizing acrylamide or a derivative thereof in the presence of two or more polar organic solvents. Examples of the two or more polar organic solvents employed in the present invention are: methanol, ethanol, 1-propanol, 2-propanol, isobutanol, t-butanol, and other alcohols, pyridine, tetrahydrofuran, dioxane, acetone, acetonitrile, dimethylformamide, dimethylacetamide, dimethylsulfoxide, N-methylpyrrolidone, and hexamethylphosphamide.

The electrophoretic gel of the present invention is obtained by polymerizing an acrylamide derivative in the presence of the polar organic solvents. When an acrylamide derivative is polymerized and two or more polar organic solvents are similarly provided in the gaps of the polymer obtained, the effect of the object of the present invention is not achieved. Nor is the effect of the object of the present invention achieved when only one polar organic solvent is employed in polymerization.

Although the combination of the two or more polar organic solvents employed is not specifically limited, a preferred example is a combination of formamide and an alcohol, preferably the combination of formamide and methanol.

Although the acrylamide derivative employed in polymerization is not specifically limited, examples are N,N'-dimethylacrylamide and N-(hydroxymethyl)acrylamide. The acrylamide derivative may be employed singly or in combinations of one or more. Polymerization initiators that are commonly employed in the polymerization of acrylamide derivatives may be employed without alteration. The concentration (W/V %) of the gel may be suitably determined by considering the molecular weight and the like of the nucleic acid to a be separated. However, it is normally set within a range of 3–10 W/V %, preferably about 5 W/V %.

The method of manufacturing the electrophoretic gel of the present invention is described in greater detail below.

The preparation of a gel at a scale of 100 ml using methanol and formamide as the polar organic solvent will be described. A flask or beaker equipped with a stirring bar is prepared. First, 36 g of urea to make a final concentration of 6 M, 25 ml of pure water (preferably milli-Q processed pure water), 15 ml of ×10 tris-boric acid-EDTA buffer solution (referred to hereinafter as "TBE", in this case ×10 TBE), and 10 ml of acrylamide derivative in the form of Long Ranger (U.S. firm FMC) are sequentially added and stirred at room temperature until the urea dissolves. The urea is added as a denaturing agent for nucleic acids or the like; it may be omitted. Urea can be added within a concentration range of 0–8 M. When the concentration of urea exceeds 6 M, the presence of polar organic solvents tends to make the urea precipitate out at low temperatures (0–10° C.). Next, while continuously stirring, the polar organic solvents in the form of 10 ml of methanol and 10 ml of formamide are admixed to adjust the final quantity to 100 ml and stirring is continued. In the present example, the final concentrations of methanol and formamide are 10 percent each. However, the concentration of the polar organic solvents is not limited thereto and may be suitably determined in consideration of the characteristics of the nucleic acid to be separated or the like. For example, a range of 5–15 percent may be set. Further, the concentration of the two or more polar organic solvents do not have to be identical. They may be suitably varied.

As needed, a water-soluble polymer in the form of dextran or some other cellulose derivative may be added to the electrophoretic gel of the present invention. The addition of water-soluble polymers increases the flexibility of the gel (Katsunori ATZAWA, Tanpakushitu-kakusan-koso 43 (1998) 2191–2198). The water-soluble polymers are added in a quantity of 1–30 (W/V) %, preferably about 2–5 (W/V) %. The water-soluble polymers are added to the reaction solution obtained above and suitably stirred to uniformly disperse and dissolve them into the reaction solution.

Minute debris in the reaction solution obtained above is desirably removed. This is because failure sometimes occurs due to the presence of minute debris in electrophoresis in capillary columns. For example, to remove the minute debris in the reaction solution, suction filtration employing a filter (0.22 microns) can be used. However, this is not a limitation.

Once impurities have been removed, the reaction solution is cooled with ice with stirring to inhibit polymerization of the gel. A low temperature chamber may be employed in place of cooling with ice. Once thorough cooling has been confirmed, a suitable amount of ammonium persulfate solution is added as a polymerization initiator. Degassing is conducted as necessary. About 0.5 ml of a 10 percent solution of ammonium persulfate solution can be added. However, this is not a limitation. Degassing of the reaction solution can be conducted, for example, for about 30 min at reduced pressure while stirring the reaction solution. Once the ammonium persulfate solution has been added and degassing has been conducted as necessary, 0.05 ml of a polymerization accelerator in the form of N,N,N',N'-tetramethylethylenediamine ("TEMED" hereinafter) is added to the reaction solution. Once the TEMED has been added, degassing is desirably conducted for another 5–10 min with stirring. At the point in time where the polymerization accelerator is added, polymerization begins rapidly and gelling commences. Accordingly, conducting the above-described steps with ice cooling or in a low-temperature chamber as set forth above is desirable from the viewpoint of inhibiting gelling prior to packing capillary columns or the like.

Preparation of the Support Member

The material, diameter, length, and the like of the support member employed in the electrophoretic gel of the present invention, as is the case for the support member employed in the above-described method of preparing an electrophoretic support, are not specifically limited. For example, support members commonly employed in multicapillary DNA sequencers may be employed. Additionally, slab gel type support members may be employed. The interior surface of the support member is preferably prepared according to the method of preparing an electrophoretic support of the present invention prior to use.

Packing of Gel into Support Member

The packing of the support member (capillary member) with the reaction solution in which gelling has been started by the addition of the polymerization initiator can be done with a gel packing device such as a GVT unit (from Shimadzu corporation) at room temperature. However, the type of gel packing device is not limited thereto. When a GVT unit is employed as the gel-packing device, the unit is put into pressure mode and all of the capillary columns are filled with solution (reaction solution that has started gelling). The filling of the capillary columns with the gelling solution is confirmed and one to two minutes later the pressure mode is released. The capillary columns that have been filled with gelling solution are left standing for about 3 hours, for example, at room temperature to complete polymerization, after which they are ready for use.

In the case of a slab gel, the same method as is conventionally employed is used to add polymerization initiator, starting gelling. The reaction solution is then packed into the support member (gel plates) and left standing for a prescribed period at room temperature to complete the manufacturing process.

Method of Electrophoresis Employing the Gel of the Present Invention (Mode 4)

The present invention further covers the method of electrophoresis in which nucleic acid or PNA fragments are separated in the presence of polar organic solvents using the support (gel) prepared by the method of preparation of the present invention or the above-described gel of the present invention. The nucleic acid that is separated may be either RNA or DNA. The gel employed in the method of electrophoresis employing the gel of the present invention may also be the matrix prepared by the method of preparation of the present invention (Mode 1). Electrophoresis employing as gel the matrix prepared in this manner is preferable because it permits the separation of longer strands of base pairs.

For example, TBE or the like to which has been added a polar organic solvent is employed as the buffer solution in electrophoresis. Examples of TBE are 0.5–5×, preferably a final concentration of 1.5×. There are no specific limitations on the type, combination, or quantity of polar organic solvent. However, as in the case of manufacturing gel, the use of two or more polar organic solvents is preferred. More preferably, a mixed solution of an alcohol and formamide, and still more preferably, a mixture of methanol and formamide is employed. The concentration of the polar organic solvent is, for example, 5–15 percent, preferably 10 percent (V/V). When using two or more polar organic solvents, the final concentration of each of the solvents is 5–15 percent, preferably 10 percent (V/V). The injection of the sample can be conducted under the same conditions as are normally employed in electrophoresis. For example, in the case of capillary columns, 5–600 seconds at 0.1–10 kV, preferably 90 seconds at 2 kV, is suitable. Migration is suitably conducted at 20–70° C., preferably 55° C., and 1–20 kV, preferably 4.8 kV. In the case of a slab gel, as well, loading can be performed by the usual methods.

Detection of the Separated Matter

Samples that can be separated by an electrophoresis method employing the electrophoretic gel of the present invention are desirably PNA fragments or nucleic acids such as DNA or RNA that have been fluorescent-labeled with a rhodamine compound so as to permit the ready detection of separated matter. However, there is no limitation to such samples; samples labeled with radioactive isotopes may also be separated. The bands of fluorescent-labeled DNA and RNA can be detected using the laser light source and fluorescent light detector of the capillary sequencer. The light source and detector of the sequencer can be employ for slab gels, as well.

EMBODIMENTS

The present invention is further described below through embodiments.

The individual resolution (Rs) in the embodiments was calculated using the signal wavelength as the Gauss pattern from the following equation using separation data.

$$Rs=(21\ln 2)^{1/2}(t_B-t_A)/(W_A+W_B)$$

Here, $t_A$ and $t_B$ denote the times at which the peak A and B signals were detected and $W_A$ and $W_B$ denote the signal widths at half the peak height of the A and B signals, respectively.

Embodiment 1

A gel matrix (100 ml) was prepared by sequentially mixing together while continuously stirring at room temperature the following reagents:
1) 35 g of urea (final concentration 6 M)
2) 25 ml of pure water (milli-Q processed water)
3) 15 ml of ×10 TBE buffer solution
4) 10 ml of Long Ranger (U.S. FMC Co.) (added after dissolution of the urea)
5) 10 ml of methanol
6) 10 ml of formamide The above are admixed, the volume is adjusted to 100 ml with milli-Q pure water, and thorough stirring is conducted again. Filtering (0.22 micron) is conducted at room temperature under negative pressure cooling with ice (10 min) is conducted with stirring, and the solution is left standing in a low-temperature chamber (30 min).

7) 0.5 ml of 10 percent (w/v) ammonium persulfate

While stirring the solution with ice cooling or in a low-temperature chamber, the stated quantity of a newly prepared batch of this reagent is added. Degassing is then conducted for 30 min with stirring.

8) 0.05 ml of TEMD

This reagent is added quickly and further degassing is conducted for about 10 min with ice cooling or in a low-temperature chamber with constant stirring.

The gel of the solution thus obtained was packed at room temperature into capillaries (SGE Co., internal diameter 100μ, external diameter 360μ, made of fused silica, total length 48 cm) using a GVT unit (Shimadzu Corporation). After packing, the capillaries were left standing for 3 hours at room temperature, yielding capillary columns filled with the gel of the present invention. These capillary columns were then employed in electrophoresis.

Sample Injection

DNA fragments that have been fluorescence-labeled by cycle sequencing or the like are purified by desalting or ethanol precipitation. Formamide or a mixed solution of formamide and buffer solution is admixed to the sample and high-temperature processing (95° C., 2 min) is conducted. A voltage was applied for from 5 seconds to 5 minutes at a range of 5–100volts per centimeter of length of the capillary to inject the sample into the capillary through the capillary inlet on the cathode side.

Electrophoresis

The following components were continuously stirred at room temperature to prepare the electrophoretic buffer solution.
1) 325 ml of pure water (milli-Q processed water)
2) 75 ml of ×10 TBE
3) 50 ml of methanol (special grade 137-01823 from Wako Pure Chemical Industries, Ltd.)
4) 50 ml of formamide (Gibco BRL 15515-026)

Electrophoresis was conducted under conditions of 55° C. and 4.8 kV.

Detection

An argon laser was directed through a detection window positioned near the anode side of the capillary, the fluorescent agent in the DNA sample was excited, and the fluorescent light thus generated was detected with a photomultimeter.

Results

TABLE 1

Ability of various gels to read DNA nucleotide sequences with a capillary electrophoretic device employing various gels.

| Type of Gel | Longest nucleotide sequence that could be read (number of bases) | |
| --- | --- | --- |
| | At resolution per base of 0.5 | At resolution per base of 0.25 |
| A gel | 635 | 810 |
| B gel | 500 | 590 |
| C gel | 425 | 520 |
| D gel | 545 | 625 |
| E gel | 470 | 565 |

The nucleotide sequence reading ability is given as the number of bases exhibited at resolution per base of 0.5 and 0.25 between DNA fragments differing by one base in length. Capillary tube employed: fused silica capillary made by SGE Co., outer diameter 360 microns, inner diameter 100 microns, length 48 cm. Prior to filling with gel, the interior of the tube was sequentially washed with 1 N sodium hydroxide, purified water, 1 N hydrochloric acid, and purified water.

Migration conditions: 6 kV, 55° C. A solution comprising the components of the individual gel compositions without the gel and urea was employed as the electrode solution.

Samples analyzed: Fluorescent-labeled DNA fragments obtained using M13mp18 single-strand DNA (Takara Co.) as template and conducting cycle sequencing using a BigDye™ Primer (PE Applied Biosystems Co.) Kit.

A Gel: 6 M urea, 10 percent (V/V) formamide, 10 percent (V/V) methanol, 10 percent (V/V) Long Ranger™, ×1.5 TBE.

B Gel: 6 M urea, 20 percent methanol, 10 percent Long Ranger™, ×1.5 TBE

C Gel: 6 M urea, 20 percent formamide, 10 percent Long Ranger™, ×1.5 TBE

D Gel: 6 M urea, 10 percent Long Ranger™, ×1.5 TBE

E Gel: 6 M urea, 10 percent Long Ranger™, ×1 TBE

TABLE 2

Ability to read DNA nucleotide sequences with a capillary electrophoretic device employing various gels and electrode solutions

| Type of gel | Type of electrode solution | Longest nucleotide sequence that could be read (number of bases) | |
|---|---|---|---|
| | | At resolution per base of 0.5 | At resolution per base of 0.25 |
| A Gel | 10 percent (V/V) formamide 10 percent (V/V) methanol and ×1.5 TBE | 635 | 810 |
| A Gel | ×1.5 TBE | 520 | 650 |
| D Gel | 10 percent (V/V) formamide 10 percent (V/V) and 1.5 TBE | 555 | 640 |
| D Gel | ×1.5 TBE | 545 | 625 |

The nucleotide sequence reading ability is given as the number of bases exhibited at resolution per base of 0.5 and 0.25 between DNA fragments differing by one base in length. Capillary tube employed: fused silica capillary made by SGE Co., outer diameter 360 microns, inner diameter 100 microns, length 48 cm. Prior to filling with gel, the interior of the tube was sequentially washed with 1 N sodium hydroxide, purified water, 1 N hydrochloric acid, and purified water.

Migration conditions: 6 kV, 55° C.

Samples analyzed: Fluorescent-labeled DNA fragments obtained using M13mp18 single strand DNA (Takara Co.) as template and conducting cycle sequencing using a BigDye™ Primer (PE Applied Biosystems Co.) Kit.

A Gel: 6 M urea, 10 percent (V/V) formamide, 10 percent (V/V) methanol, 10 percent (V/V) Long Ranger™, ×1.5 TBE.

D Gel: 6 M urea, 10 percent Long Ranger™, ×1.5 TBE

Table 1 compares the conditions under which the polar organic solvents were present during gel production and improvements in the ability to read nucleotide sequences of the gels. As is evident from the embodiment employing formamide and methanol, at least two polar organic solvents were required; the effect was not achieved with just one. Further, to the extent investigated, the optimal concentration of the two organic solvents was 10 percent (v/v) each. Under these conditions, it was sometimes possible to read 900 bases or more.

Table 2 shows whether or not a polar organic solvent was present during gel production, whether or not a polar organic solvent was present in the buffer solution used in electrophoresis, and how the ability of the gels to read nucleotide sequences was affected. As is clear from these tables, the best results were achieved when the organic solvents were present both during gel preparation and during electrophoresis.

Embodiment 2

Support Member Employed

In the method of preparing an electrophoretic support of the present invention, 384 fused silica capillary columns from Moritex Co. were employed as the support member. These capillary columns were 48 cm in length, had a length of 39.5–40 cm from inlet to detection window, measured 100 μm in inner diameter and 300 μm in outer diameter, and had uncoated internal surfaces.

Washing

Washing was sequentially conducted at room temperature with 0.1 M $NaHCO_3$ (pH 9.0), pure water (milli-Q processed water), 1 M HCl, and pure water (milli-Q processed water). For comparison, washing was also sequentially conducted by the conventional method with 1 M NaOH (pH 13–14), pure water (milli-Q processed water), 1 M HCl, and pure water (milli-Q processed water). Washing with each solution lasted for 3 minutes.

Preparation of Matrix (Gel) and Injection into Column

Gel matrices (100 ml) were prepared in 385 of the above-described washed fused silica capillary columns First, acrylamide/bis, the commercial product Long Ranger (U.S. FMC Co.), or Page Plus (Amresco Co.) monomer solution were used to prepare the gel matrices. The composition of the solution prior to polymerization was as follows.

1) 4 percent (w/v) (acrylamide (5 percent crosslinked with bisacrylamide)/7 M urea/×1 TBE buffer solution
2) 4 percent (w/v) (acrylamide (5 percent crosslinked with bisacrylamide)/10 percent (v/v) formamide/10 percent (V/V) methanol/7 M urea/×1 TBE buffer solution
3) 10 percent (V/V) (Page Plus (Amresco Co.)/7 M urea/×1DBE
4) 10 percent (V/V) (Page Plus (Amresco Co.)/formamide/10 percent (V/V) methanol/7 M urea/×1TBE)
5) 10 percent (V/V) (Long Ranger (U.S. FMC Co.)/7 M urea ×1 TBE)
6) 10 percent (V/V) (Long Ranger (U.S. FMC Co.)/formamide/10 percent (V/V) methanol/7 M urea/×1 TBE)

A quantity of TEMED yielding a final concentration of 0.06 percent (V/V) was added to the solution of the above-stated composition prior to polymerization and degassing was conducted for 30 min while cooling with ice. A quantity of ammonium persulfate yielding a final concentration of 0.05 percent (W/V) was then added and the solution was further degassed for 5 min.

At the point when the polymerization reaction began, each of the 384 capillary columns was filled with gel by the same method as in Embodiment 1 and the capillary columns were placed at room temperature.

Separately from the above-described gel preparation, standard samples for sequencing (pGEM-3Zf(+)/21M13 forward primer) and fluorescent-labeling agent (BigDye terminator) were prepared.

Electrophoresis

Sequencing (electrophoresis) was conducted with the gel-filled capillary columns and a RISA sequencer (Shimadzu Corporation) at an applied voltage of 4.8 kV and a temperature of 50° C. The conditions were identical to those in Embodiment 1

Results

TABLE 3

| Gel Composition | Alkali Solution Used for washing | Maximum Base Number At resolution per base of 0.5 |
|---|---|---|
| Acrylamide-bis | NaHCO$_3$ | 560 |
| Acrylamide-bis | NaOH | 520 |
| Acrylamide-bis/ formamide/methanol | NaHCO$_3$ | 830 |
| Acrylamide-bis/ formamide/methanol | NaOH | 750 |
| Page Plus | NaHCO$_3$ | 750 |
| Page Plus | NaOH | 560 |
| Page Plus/formamide/ methanol | NaHCO$_3$ | 850 |
| Page Plus/formamide/ methanol | NaOH | 750 |
| Long Ranger | NaHCO$_3$ | 750 |
| Long Ranger | NaOH | 540 |
| Long Ranger/ formamide/methanol | NaHCO$_3$ | 1,200 |
| Long Ranger/ formamide/methanol | NaOH | 1,000 |

Note: All gels contained 7M urea and x1 TBE.
The number of bases is the value at a resolution per base of 0.5

As shown in Table 3, when the gel comprised Page Plus, for example, and washing was conducted with 0.1 M NaHCO$_3$, 750 nucleotide sequences were read at a resolution per base of 0.5. This roughly matches the number of nucleotide sequences that can be read with a RISA sequencer. By contrast, when washing was conducted with 1 M NaOH, only 560 nucleotide sequences could be read at a resolution per base of 0.5. Comparing gels of solutions of identical composition prior to polymerization shows that regardless of the type of gel, washing with 0.1 M NaHCO$_3$ permitted the reading of longer strands of nucleotide sequences than when washing was conducted with 1 M NaOH.

Further, when a single washing solution was employed, gels containing both formamide and methanol permitted the reading of longer strands of nucleotide sequences than gels that did not contain formamide and methanol.

Further, even when washing was conducted with either 0.1 M NaHCO$_2$ or 1 M NaOH, gels containing both formamide and methanol permitted the reading of longer strands of nucleotide sequences than gels that did not contain both.

From the results of the presence of both formamide and methanol in the gels, it was found that the use of 0.1 M NaHCO$_3$ had a synergistic effect on washing.

No bubbles were seen for any type of gel in the capillary column when processed with 0.1 M NaHCO$_3$. When 0.1 M NaHCO$_3$ (pH 9.0) was employed in washing, safety increased for work factors such as handling relative to the use of 1 M NaOH.

What is claimed is:

1. A method for preparing an electrophoretic separation article comprising:
    i) providing a support comprising a silicon-containing material and washing at least a portion of a surface of said support for contacting an electrophoretic matrix with a weakly alkaline solution; and
    ii) filling or coating said support with an electrophoretic matrix;
    thereby obtaining an electrophoretic separation article;
    in which the electrophoretic matrix is a composition comprising acrylamide or a derivative thereof or a polymer thereof, and at least two organic solvents.

2. An electrophoretic gel comprising a polyacrylamide polymer or a polymer comprising an acrylamide derivative, and two or more organic solvents, in which one of the organic solvents is formamide.

3. The electrophoretic gel of claim 2, in which a second organic solvent is an alcohol.

4. The electrophoretic gel of claim 3, in which the alcohol is methanol.

5. The electrophoretic gel of claim 2, which further comprises a water-soluble polymer.

6. The electrophoretic gel of claim 5, in which the water-soluble polymer is a dextran, polyethylene glycol or cellulose.

7. A process for preparing an electrophoretic gel comprising polymerizing a composition comprising acrylamide or a derivative thereof in the presence of at least two organic solvents.

8. The process of claim 7, in which the composition comprises a derivative of acrylamide that is N,N'-dimethylacrylamide or N-(hydroxymethyl)acrylamide.

9. The process of claim 7, in which one of the organic solvents is an alcohol.

10. The process of claim 9, in which the alcohol is methanol.

11. The process of claim 9, in which a second organic solvent is formamide.

12. The process of claim 7, in which one of the organic solvents is formamide.

13. The process of claim 7, in which the composition further comprises a water-soluble polymer.

14. The process of claim 13, in which the water-soluble polymer is a dextran, polyethylene glycol or cellulose.

15. A process for electrophoretic separation of a sample comprising applying said sample to an electrophoretic separation article comprising an electrophoretic gel comprising a polyacrylamide polymer or a polymer comprising an acrylamide derivative, and two or more organic solvents, and separating the sample by applying an electric field electrophoretic separation article.

16. The process of claim 15, in which the electrophoretic gel further comprises a dextran, polyethylene glycol or cellulose.

17. The process of claim 15, in which the sample comprises a nucleic acid or a peptide nucleic acid.

18. The method of claim 15, in which the sample comprises a DNA or a RNA.

19. The method of claim 15, in which the organic solvent comprises formamide or an alcohol or a mixture thereof.

20. The method of claim 19 in which the alcohol is methanol.

* * * * *